July 16, 1946. F. WURZLOW, SR Plant Pat. 708
LILY PLANT
Filed Nov. 5, 1945
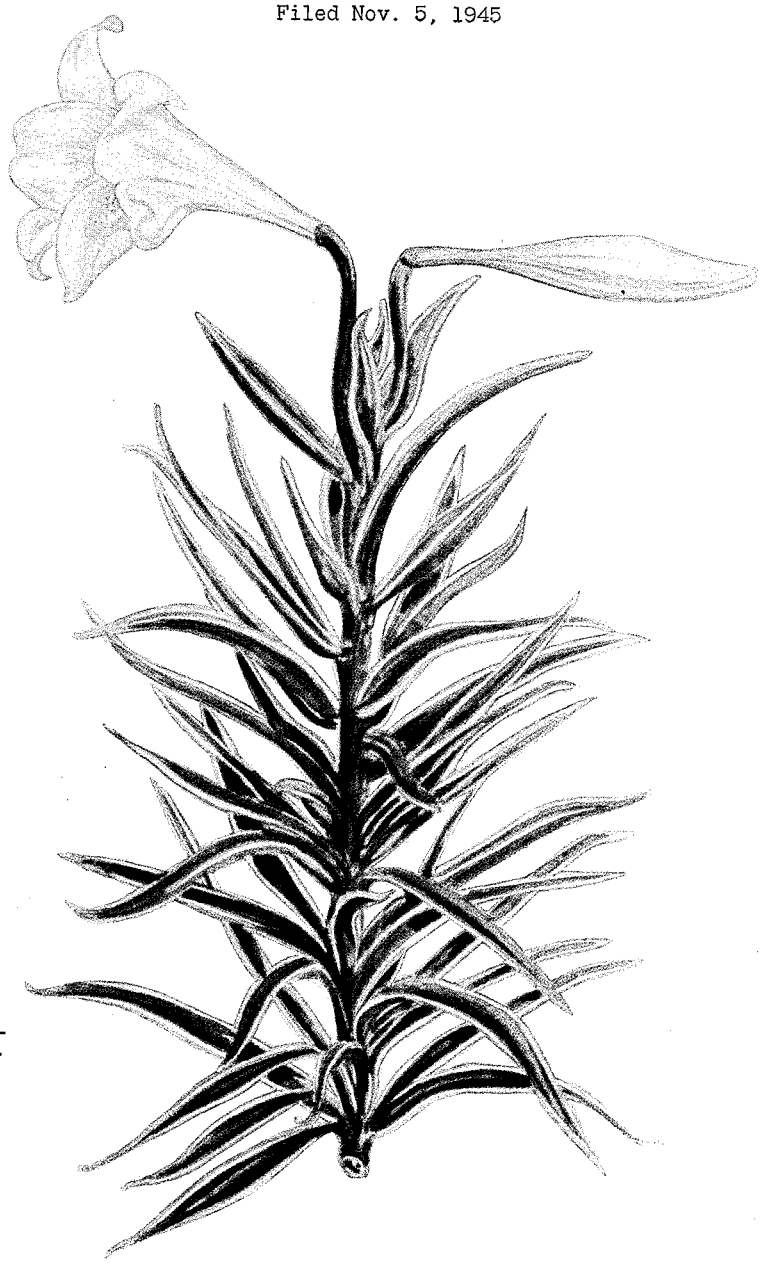
Fig. I.
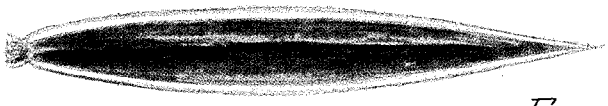
Fig. 2.
INVENTOR.
Frank Wurzlow, Sr.
BY
Wilfred E. Lawson
ATTORNEY.

Patented July 16, 1946

Plant Pat. 708

UNITED STATES PATENT OFFICE

708

LILY PLANT

Frank Wurzlow, Sr., Houma, La.

Application November 5, 1945, Serial No. 626,743

1 Claim. (Cl. 47—60)

This invention relates to a new type or variety of lily plant and relates specifically to that type known as the Creole Easter lily, or usually identified as *Lilium longiflorum*.

The present invention is characterized by the distinctive leaf coloration, each leaf having a white or silver fringe around it.

The plant is also characterized by the fact that the stalk appears to be more bushy, the plant does not grow so tall as the ordinary Creole Easter lily.

In the illustration of the plant forming a part of this specification:

Figure 1 shows the actual leaf foliage and blossom, showing the bushy character of the plant;

Figure 2 is a plan view of a leaf showing the distinctive white or silvery white bordering.

The history of the discovery and development of the present improved Creole Easter lily is as follows.

I have been growing Creole Easter lily bulbs commercially for the past twelve years. About two years ago the herein disclosed new variety of lily appeared as a sport in my lily field, the only one of its kind among approximately one hundred thousand bulbs.

After this sport blossomed, it was potted and later transferred back to the field and the following season the original bulb was replanted together with the stem bulbs and there have now been produced in all twenty-four plants, all true to the mother plant.

The main features of this new variety of Creole Easter lily are that each leaf has a white or silver fringe around it; the stalk appears to be more bushy than the original Creole Easter lily and it does not appear to grow as tall. The largest of the plants produced this year had six blossoms which appeared to be substantially the same as the blossoms of the ordinary Creole Easter lily.

These new characteristics as here illustrated and explained, actually represent a distinct and new reproducible variety of Creole Easter lily as is evident by the fact that all of the bulblets obtained from the original sport plant developed to the flowering stage and have uniformly produced plants having the characteristics described and claimed herein.

What I claim as new and wish to secure by Letters Patent is:

The herein disclosed and described variety of Creole Easter lily plant characterized by the fact that each of the leaves has a bordering fringe of white or silver; the stalk is more bushy; it does not grow so tall as the ordinary Creole Easter lily, and as many as six blossoms may be produced upon one plant.

FRANK WURZLOW, Sr.